United States Patent [19]

Chandler et al.

[11] 4,039,666

[45] Aug. 2, 1977

[54] ANTICONVULSANT PHENYLSILANES

[75] Inventors: Michael L. Chandler; Robert H. Krahnke; Robert R. LeVier, all of Midland, Mich.

[73] Assignee: Dow Corning Corporation, Midland, Mich.

[21] Appl. No.: 727,091

[22] Filed: Sept. 27, 1976

Related U.S. Application Data

[63] Continuation of Ser. No. 640,987, Dec. 15, 1977, abandoned.

[51] Int. Cl.$^2$ .................................................. A61K 31/695
[52] U.S. Cl. ............................................................. 424/184
[58] Field of Search .................................................. 424/184

[56] References Cited

U.S. PATENT DOCUMENTS

| | | | |
|---|---|---|---|
| 3,651,115 | 3/1972 | Belsky et al. | 424/184 |
| 3,853,994 | 12/1974 | Barcza | 424/184 |

*Primary Examiner*—Sam Rosen
*Attorney, Agent, or Firm*—Howard W. Hermann

[57] ABSTRACT

Suppression of convulsions in warm-blooded animals is accomplished by administration of phenylsilanes of the formulas $\phi R_2SiX$, $\phi RSiX_2$, $\phi SiX_3$, $\phi_2RSiX$, and $\phi_3SiX$ in which R is an alkyl or alkenyl group and X is a hydroxyl group or one of several readily hydrolyzable radicals, such as the methoxy group. It should be understood that where there is more than one R or one X group in a composition, they need not be the same species.

13 Claims, No Drawings

ANTICONVULSANT PHENYLSILANES

This is a continuation of application Ser. No. 640,987, filed Dec. 15, 1975, now abandoned.

The present invention relates to a method of suppressing convulsions in warm-blooded animals. In one aspect the invention relates to a method of combating epileptic seizures.

This invention is based on the unexpected findings that certain phenylsilanes, when administered to warm-blooded animals, exhibit anticonvulsant activity. "Anticonvulsant activity," of course, is the ability of a compound to terminate or arrest convulsive episodes—or, in a further sense, to prevent or suppress the incidents of convulsive seizures in patients, such as those suffering from epilepsy.

Thus, the present invention provides a method of suppressing convulsions in a warm-blooded animal which comprises administering to such an animal a silane of the formulas $\phi R_2SiX$, $\phi RSiX_2$, $\phi SiX_3$, $\phi_2RSiX$, $\phi_3SiX$, in which X is a hydroxyl group of radical which is capable of hydrolyzing in vivo to form the hydroxyl group, $\phi$ is the phenyl group, and R is an alkyl, or alkenyl such as methyl, vinyl, allyl, ethyl, butyl or hexyl group; said silane being administered in amounts sufficient to suppress convulsions in the animal. It should be understood that where there is more than one R or one X group is a composition they need not be the same species. It is preferred that the R group contain 1 to 6 carbon atoms.

The phenylsilanes useful in the practice of the above-described method are $\phi Si(OH)_3$, $\phi(CH_3)Si(OH)_2$ and $\phi(CH_3)_2SiOH$ and certain silanol precursors such as $\phi Si(OCH_3)_3$, $\phi(CH_3)Si(OCH_3)_2$, $\phi(CH_3)_2SiOCH_2CH_3$, $\phi(CH_2CH_3)Si(OCH_2CH_3)_2$, $\phi(CH=CH_2)Si(OCH_2CH_3)_2$. These silanol precursors contain silicon-bonded radicals which hydrolyze in the gastrointestinal tract or bloodstream to give rise to the active phenylsilanols. Hydrolyzable groups attached to organosilicon compounds are numerous and well known in the art. Generally, these groups are organic moieties such as hydrocarbonoxy radicals, however, other groups such as $NH_2$ do not fit the classic definition of "organic." Those radicals which hydrolyze (or react with water) in vivo to form the $\equiv$SiOH, include the hydrogen atom, alkoxy radicals of the formula —OR′ in which R′ is an alkyl of from 1 to 3 inclusive carbon atoms and acyloxy radicals of the formula $$-\underset{\underset{O}{\|}}{O}CR''$$

in which R″ is an alkyl radical or an aryl-containing monovalent hydrocarbon radical, including aryl, alkylaryl and arylalkyl groups. Further examples of readily hydrolyzable groups are amine radicals of the formula —NR′″$_2$ in which R′″ is a hydrogen atom or an alkyl or aryl-containing hydrocarbon radical as described above; aminoxy radicals of the formula —ONR′″$_2$; ketoxime radicals of the formula —ON=CR′$_2$, amido radicals of the formula

amidino radicals of the formula

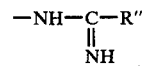

and thioamide radicals such

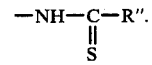

In addition to $\equiv$SI—O—C and $\equiv$Si—N—bonding, the $\equiv$SI—S—bond is hydrolyzable, with sulfur-containing hydrolyzable groups being represented by radicals of the formulae —SR″,

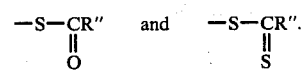

It is apparent from this listing that the $\equiv$Sic—bond does not react with water and radicals such as —CH$_3$ and —C$_6$H$_5$ are not considered "hydrolyzable groups." It is also to be noted that certain groups which hydrolyze very slowly or only under extreme conditions do not hydrolyze in vivo at a rate sufficient to provide silanol or exhibit aniticonvulsant activity. The butoxy radical is one such group. To provide miscibility and solubility in liquid pharmaceutical carriers it is preferred that the R″and R′″hydrocarbon radicals are alkyl radicals of 1 to 20 carbon atoms or aryl-containing monovalent hydrocarbon radicals of from 6 to 12 carbon atoms.

The above listing of readily hydrolyzable radicals is not intended to be all inclusive. Other such hydrolyzable radicals, such as cyclized acyloxy, mercapto, and amines; for example

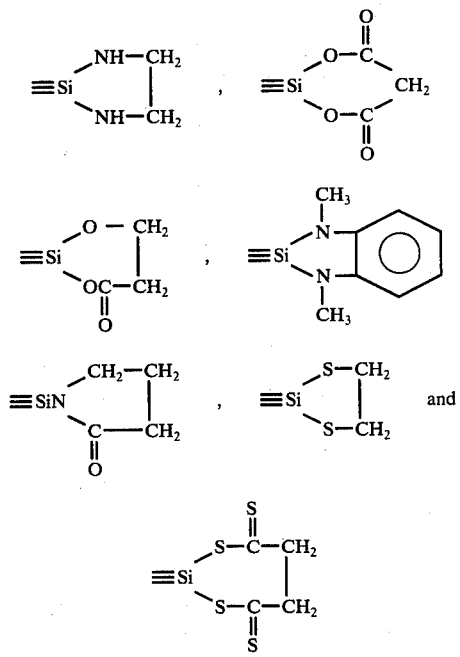

are also available. Exemplary of the preferred and most readily available silanes are $\phi Si(OH)_3$, $\phi Si(OCH_3)_3$, $\phi(CH_3)_2SiOH$, $\phi(CH_3)_2SiOCH_2CH_3$, $\phi(CH_3)Si(OH)_2$, $\phi CH_2CH_3)Si(OCH_2CH_3)_2$, and $\phi(CH=CH_2)Si(OCH_2CH_3)_2$. In view of the well devel-

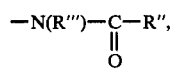

oped state of the art relating to organosilanes, further description would be "repetitious."

The phenylsilanes are readily synthesized by well known techniques. Hydrolysis of the corresponding chlorosilane gives rise to the silanol compounds. Similarly the chlorosilanes can be converted to the desired silanol precursors by a chlorine displacement reaction with the appropriate organic compound. For example, phenylmethyldichlorosilane is reacted with the corresponding alcohol to obtain the described dialkoxy silanes. Phenylmethyldichlorosilane can alternatively by hydrolyzed in the presence of an acid acceptor to obtain the described phenylmethylsilanediol. Phenylmethylsilanediol is a crystalline solid, while the hydrolyzable silanes are typically liquids.

The defined silanes can be administered in any pharmaceutically accepted manner by either the oral or parenteral route. The dose form of the silane can include pharmaceutically acceptable carriers and other conventional adjuvants. The dosage may be administered orally in such forms as tablets, capsules, suspensions and the like or parenterally in the form of an injectable suspension or solution. Suitable pharmaceutical carriers include liquids, such as water or oils which may be of animal, vegatable or synthetic origin, for example, peanut oil, mineral oil, sesame oil and the like; aqueous dextrose and related sugar solutions and glycols, such as propylene glycol. Inert solid carriers, such as calcium carbonate, calcium phosphate, starch, lactose and the like can also be utilized. Other pharmaceutical carriers are listed in "Remington's Pharmaceutical Sciences" by E. W. Martin, a well known reference in this field.

The silanes are administered in amounts effective to suppress convulsions in warm-blooded animals, such as mice, rats, gerbils, dogs, monkeys and humans. The optimum anticonvulsant amount will vary with the particular silane (or mixtures thereof) utilized, with the size and species of animal treated, and with the severity, both as to duration and frequency, of the convulsive episodes suffered by the animal. Dosages of about 10 to 1000 mg./kg. of body weight are generally sufficient to prevent or reduce the incidence of convulsive seizures. Suggested unit dosages for larger animals are 100 to 1000 mg. of silane per tablet or capsule or 25 to 300 mg. of silane/cc. of solution or dispersion. In any event, the effective amount is well below the toxic amount ($LD_{50}$) of the silane compound. The effective amount is also well below those amounts which give undesirable neurological side effects, such as sedation.

The following examples are illustrative of the anticonvulsant activities of the phenylsilanes utilized in the practice of the present invention.

EXAMPLE 1

The electroshock test procedure was used to determine anticonvulsant activities of diphenylmethylsilanol. Adult male mice (Carworth CF 1 strain) were utilized as test animals. With administration of a 0.1 sec. Train of pulsing DC shocks each of 1 millisecond duration, 150 volts at 100 Hz through corneal-temporal electrodes, all untreated mice demonstrated tonic extension of the hind limbs. Seizure protection was scored as inhibition of tonic extension. Groups of mice (six/group) were dosed orally with varying amounts of diphenylmethylsilanol in a sesame oil suspension. The dosages ranged from 10 to 1000 mg./kg. and the train of electric shocks was applied 2, 4 and 6 hours after dosing. The effective dose to prevent convulsions in half the animals ($ED_{50}$) was determined at 2, 4 and 6 hours to be 52, 63, 100 mg/kg, respectively, and the 95 percent CI (confidence interval) was 23 to 114 mg./kg.; 27 to 141 mg./kg.; 47 to 212 mg./kg.

EXAMPLE 2

The electric shock test procedure was also used to determine anticonvulsant activities of phenylmethyldimethoxysilane. Adult male mice (Carworth CF 1 Strain) were utilized as test animals. With administration of a train of pulsing DC shocks each of 1 millisecond duration, 150 volts at 100 Hz through corneal-temporal electrodes, all untreated mice demonstrated tonic extension of the hind limbs. Seizure protection was scored as in Example 1. Groups of mice ten/group) were dosed orally with varying amounts of phenylmethyldimethoxysilane in a sesame oil solution. The dosages ranged from 25 to 200 mg./kg. and the train of electric shocks was applied ½, 1, 1½, 2 and 3 hours after dosing. The effective dose to prevent convulsions in half the animals ($ED_{50}$) was determined at ½, 1, 1½, 2 and 3 hours to be 52, 86, 64, 82 and 90 mg./kg., respectively. Utilizing the same electroshock test procedure as set forth in the first paragraph of this example, groups of mice (ten/group) were dosed intraperitoneally with varying amounts of phenylmethyldimethoxysilane in a sesame oil solution. The dosages ranged from 25 to 200 mg./kg. and the train of electric shocks was applied ½, 1, 1½, 2 and 3 hours after dosing. The effective dose to prevent convulsions in half the animals ($ED_{50}$) was determined at ½, 1, 1½, 2 and 3 hours to be 45, 65, 52, 51 and 70 mg./kg., respectively.

EXAMPLE 3

The electric shock test used in Example 1 and 2 was used in determining the anticonvulsant activities of several other silanes.

Results of $ED_{50}$ for the various silanes are tabulated in Table 1 and $LD_{50}$'s for representative silanes shown in Table 2.

As a test of relative sedative activity of the various silanes, the ability of each to potentiate the action of hexobarbital was studied. For each silane, two groups of male mice (Carworth $CF_1$ strain) were utilized as test animals. Two groups of mice (six/group) were used, one group was orally dosed with 316 mg./kg. of the test silane in sesame oil carrier 90 minutes before administration of hexobarbital. Hexobarbital was administered by intraperitoneal injection of 100 mg./kg. in saline carrier. The time from loss of the righting reflex to recovery of the righting reflex was recorded as sleep time. Potentiation of hexobarbital of the test silane is the ratio of the mean sleep time by the group of test animals dosed with the silane divided by the mean sleep time of the control group not dosed with silane.

TABLE I
Anticonvulsant Activity of Various Silanes

| Class | $R_1$ | $R_2$ | X | Time After[1] Dosing (Hours) | MES[2] $ED_{50}$ (mg/kg) | Protection[3] vs. Pentylenetetrazol | Potentiation[4] of Hexobarbital |
|---|---|---|---|---|---|---|---|
| $\phi_2\text{Si}-\text{X}$ \| $R_1$ | —CH$_3$ | — | —OH | 2<br>4<br>6 | 52<br>63<br>100 | 3/6 | 1.5 |
| $R_1$ \| $\phi-\text{Si}-\text{X}$ \| $R_2$ | —CH$_3$ | —CH$_3$ | —OH | 2<br>4<br>6 | 118<br>135<br>110 | 2/6 | 2.7 |
|  | —CH$_3$ | —CH$_3$ | —OC$_2$H$_5$ | 2<br>4<br>6 | 200<br>213<br>350 | 2/6 | >1.3 |
| $\phi_3\text{SiX}$ | — | — | —OH | 2<br>4<br>6 | 105<br>60<br>110 | n.p. | 1.9 |
| $\phi\text{Si}-\text{X}_2$ \| $R_1$ | —CH$_3$ | — | —OH | 2<br>4<br>6 | 80<br>110<br>80 | 2/6 | 1.8 |
|  | —CH$_3$ | — | —OCH$_3$ | 2<br>4<br>6 | 56<br>50<br>106 | 2/6 | 1.2 |
|  | —CH$_3$ | — | —OC$_2$H$_5$ | 2<br>4<br>6 | 180<br>31<br>220 | n.p. | 1.1 |
|  | —CH$_3$ | — | —OCH(CH$_3$)$_2$ | 2<br>4<br>6 | 94<br>84<br>41 | 2/6 | 1.8 |
|  | —CH$_3$ | — | —OCCH$_3$<br>‖<br>O | 2<br>4<br>6 | 200<br>125<br>142 | n.p. | 1.8 |
|  | —C$_2$H$_5$ | — | —OH | 2<br>4<br>6 | 120<br>160<br>— | 6/6 | 1.7 |
|  | —C$_2$H$_5$ | — | —OC$_2$H$_5$ | 2<br>4<br>6 | 150<br>180<br>64 | 4/6 | 1.8 |
|  | —CH=CH$_2$ | — | —OC$_2$H$_5$ | 2<br>4<br>6 | 170<br>200<br>200 | 1/6 | 0.9 |
| $\phi\text{SiX}_3$ | — | — | —OCH$_3$ | 2<br>4<br>6 | 560<br>300<br>160 | n.p. | 1.3 |
|  | — | — | —OC$_2$H$_5$ | 2<br>4<br>6 | 170<br>31<br>220 | n.p. | 2.1 |
|  | — | — | —OCH(CH$_3$)$_2$ | 2<br>4<br>6 | n.p.<br>>1000<br>800 | n.p. | 2.1 |

Explanation of Table
[1]The test silane was administered orally in sesame oil vehicle at time zero.
[2]M.E.S. - Maximal Electroshock Test - $ED_{50}$ is dose calculated to protect 50% of mice from tonic extensor convulsion. The dosages ranged from 10 to 1000 mg/kg.
[3]Pentylenetetrazol 80 mg/kg s.c. produces clonic convulsions in 90% of control mice. Values in table are the numbers of mice protected from clonic convulsion/number tested when dosed with 316 mg/kg test compound.
[4]Potentiation of hexobarbital - values are the ratios of sleep times of animals dosed with 316 mg/kg test compound plus 100 mg/kg hexobarbital to the sleep times of animals dosed with hexobarbital alone.
n.p. - no protection observed.

TABLE II
$LD_{50}$ Data [1]

| Compound | $LD_{50}$ (95% Confidence Interval) (mg/kg) |
|---|---|
| $\phi\text{Si(OCH}_3)_2$ \| CH$_3$ | 5370 (4260 – 7000) |
| $\phi\text{SiOCH}_2\text{CH}_3$ \| (CH$_3$)$_2$ | 5380 (4320 – 6770) |
| $\phi\text{Si(OCH}_2\text{CH}_3)_3$ | 5140 (4130 – 6440) |
| $\phi_2\text{SiOH}$ \| CH$_3$ | >5000[2] |

[1]Male mice, 25 gm. were used. Each compound was given orally in sesame oil at doses ranging from 648-8333 mg/kg, except $\phi_2\text{SiOH}$ \| CH$_3$ in which case the highest dose was 5000 mg/kg. The mice were observed for 14 days and the number of deaths was recorded. $LD_{50}$ values were calculated by Finney's method.

TABLE II-continued

LD₅₀ Data [1]

| Compound | LD₅₀ (95% Confidence Interval) (mg/kg) |
|---|---|

[2]No deaths were observed at any dose level used.

Reasonable modifications and variations are within the scope of the invention which is directed to a process for the treatment of animals to induce an anticonvulsant effect by administering a phenylsilane.

That which is claimed is:

1. A process for the treatment of a warm-blooded animal to induce an anticonvulsant effect, comprising administering to said animal a phenylsilane, the phenylsilane selected from the group consisting of $\phi R_2SiX$, $\phi_2RSiX$, $\phi RSiX_2$, $\phi SiX_5$, and $\phi_3SiX$ in which R is an alkyl or alkenyl group and X is a hydroxy group or a radical which hydrolyzes in vivo to form the hydroxyl group, said silane being administered in an amount effective to suppress convulsions in the animal.

2. A method as set forth in claim 1 wherein the phenylsilane is phenyldimethylsilanol.

3. A method as set forth in claim 1 wherein the phenylsilane is diphenylmethylsilanol.

4. A method as set forth in claim 1 wherein the phenylsilanes are selected from the group consisting of phenylmethylsilanediol and phenylethylsilanediol.

5. A method as set forth in claim 1 wherein the phenylsilane is selected from the group consisting of phenylmethyldimethoxysilane, phenylmethyldiethoxysilane, phenylmethyldiisopropyloxysilane, phenylmethyldiacetoxysilane, phenylethlydiethoxysilane and phenylvinyldiethoxysilane.

6. A method as set forth in claim 1 wherein the phenylsilane is phenyltriethoxysilane.

7. A method as set forth in claim 1 wherein the phenylsilane is triphenylsilanol.

8. A method in accordance with claim 1 wherein the phenylsilane is administered orally.

9. A method in accordance with claim 1 wherein the phenylsilane is administered parenterally.

10. A method in accordance with claim 9 wherein the phenylsilane is selected from the group consisting of diphenylmethylsilanol and phenylmethyldimethoxysilane.

11. A method in accordance with claim 1 wherein the phenylsilane is administered in an amount in the range from about 10 to 1000 mg/kg of animal body weight.

12. A method in accordance with claim 1 wherein the phenylsilane is administered in combination with a pharmaceutically acceptable carrier.

13. A method as set forth in claim 1 wherein R contains 1 to 6 carbon atoms.

* * * * *

UNITED STATES PATENT AND TRADEMARK OFFICE
CERTIFICATE OF CORRECTION

PATENT NO. : 4,039,666
DATED : August 2, 1977
INVENTOR(S) : M. L. CHANDLER et al.

It is certified that error appears in the above-identified patent and that said Letters Patent are hereby corrected as shown below:

Column 1, line 21, "$\phi_3 Six$" should read -- $\phi_3 SiX$ --

Column 1, line 28, "is" should read --in--.

Column 2, line 64, the word "Exemplary" should start a new paragraph.

Column 2, line 67, "$\phi CH_2 CH_3)Si(OCH_2 CH_3)_2$" should read --$\phi(CH_2 CH_3)Si(OCH_2 CH_3)_2$--.

Column 3, line 27, "vegatable" should read --vegetable--.

Column 4, line 23, "ten/group)" should read --(ten/group)--.

Column 7, line 20, "$\phi SiX_5$" should read --$\phi SiX_3$--.

Signed and Sealed this

Thirtieth Day of September 1980

[SEAL]

Attest:

SIDNEY A. DIAMOND

Attesting Officer  Commissioner of Patents and Trademarks